United States Patent [19]

Romano et al.

[11] 4,318,862

[45] Mar. 9, 1982

[54] PROCESS FOR PRODUCING DIMETHYLCARBONATE

[75] Inventors: Ugo Romano, Vimercate; Franco Rivetti, Schio; Nicola Di Muzio, Peschiera Borromeo, all of Italy

[73] Assignee: Anic S.p.A., Palermo, Italy

[21] Appl. No.: 205,949

[22] Filed: Nov. 12, 1980

[30] Foreign Application Priority Data

Dec. 4, 1979 [IT] Italy .................. 27816 A/79

[51] Int. Cl.$^3$ ............................................. C07C 69/96
[52] U.S. Cl. .................................................. 260/463
[58] Field of Search ....................................... 260/463

[56] References Cited

U.S. PATENT DOCUMENTS

| | | | |
|---|---|---|---|
| 3,846,468 | 11/1974 | Perrotti et al. | 260/463 |
| 4,113,762 | 9/1978 | Gaenzler et al. | 260/463 |
| 4,218,391 | 8/1980 | Romano et al. | 260/463 |
| 4,234,504 | 11/1980 | Hallgren et al. | 260/463 |

FOREIGN PATENT DOCUMENTS 7604857 11/1976 Netherlands .................. 260/463

*Primary Examiner*—Anton H. Sutto
*Attorney, Agent, or Firm*—Morgan, Finnegan, Pine, Foley & Lee

[57] ABSTRACT

A process for preparing dimethylcarbonate by reacting methanol with mixtures of carbon monoxide and oxygen which also contain hydrogen. The catalyst is constituted by a salt of a metal of groups IB, IIB or VIII of the periodic system, dissolved or dispersed in the reaction medium.

It has been found that the hydrogen does not interfere in the reaction, so that a hydrogen-enriched gaseous mixture (synthesis gas) is withdrawn from the reactor. It is therefore particularly advantageous in that it produces dimethylcarbonate and at the same time provides hydrogen-enriched synthesis gas.

4 Claims, No Drawings

PROCESS FOR PRODUCING DIMETHYLCARBONATE

This invention relates to a process for producing dimethylcarbonate by reacting methanol with a gaseous mixture containing carbon monoxide, hydrogen and oxygen.

Thus in order to produce dimethylcarbonate, a synthesis gas can be used consisting of carbon monoxide and hydrogen, it being unnecessary to use pure carbon monoxide.

The main advantage of the invention consists of the fact that simultaneously with the production of dimethylcarbonate, a hydrogen enrichment of the $CO/H_2$ mixture is obtained.

The applicant is familiar with a patent (Belgian Pat. No. 859,272) which relates to a process based on the reaction between an alcohol, carbon monoxide and oxygen carried out in the presence of a catalyst constituted by a salt of a metal of groups IB, IIB or VIII of the periodic system, preferably a monovalent copper salt.

It has now been surprisingly found that it is possible to carry out the same reaction using gas mixtures containing carbon monoxide and hydrogen (synthesis gas) instead of pure carbon monoxide, without the presence of the hydrogen, even at high concentration, altering the dimethylcarbonate production reaction or giving rise to secondary reactions such as could have been predicted knowing the normal reactivity of this gas.

For example, there is no water formation due to reaction between the hydrogen and the oxygen necessary for the reaction, neither is there any reduction of the alcohol or of the carbonic ester, nor is there any deactivation of the catalytic system due to reduction of the metal salt to the metal in its zerovalent state, in spite of the fact that reactions of this type are well known.

The process is therefore suitable for enriching synthesis gases of various compositions with hydrogen, while at the same time producing dimethylcarbonate to give a double advantage from the technical aspect, in that two operations of industrial interest are performed by means of a single process.

In particular, the production of the dimethylcarbonate does not require the use of pure carbon monoxide. Moreover, by this process it is possible to obtain mixtures of carbon monoxide and hydrogen of the required composition starting from mixtures which are richer in carbon monoxide, suitable for example for the synthesis of methanol, which constitutes one of the starting compounds for the synthesis of the dimethylcarbonate.

According to the process of the present invention, a mixture of carbon monoxide and hydrogen containing between 0.1 and 90% of hydrogen by volume is reacted with methanol and oxygen in the presence of a salt of a metal pertaining to groups IB, IIB and VIII of the periodic system, with the metal ion bonded to the smallest possible number of inorganic anions, preferably a copper salt. The reaction is carried out by dispersing or dissolving the metal salt in the methanol, possibly in the presence of another liquid solvent or diluent, which can be the reaction product itself, and feeding into the dispersion thus obtained the gaseous streams of carbon monoxide, hydrogen and oxygen, either mixed together or separated, and either continuously or in alternate cycles. The reaction produces dimethylcarbonate and water in accordance with the stoichiometric equation

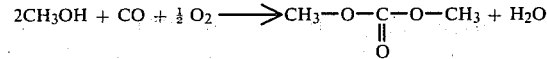

with practically quantitative absorption of the oxygen fed, and leading to hydrogen enrichment of the synthesis gas. The process can be carried out over a wide pressure and temperature range. The temperature used is preferably between 70° and 150° C., and the total pressure of the reaction system is chosen such as to give a partial pressure of carbon monoxide greater than atmospheric pressure.

The $CO/O_2$ ratio can vary widely in accordance with the required carbon monoxide content of the exit gas, which can be reduced down to 1% by volume.

In addition to the carbon monoxide and hydrogen, the feed gas can contain other gases which are insert under the reaction conditions such as nitrogen, methane or carbon dioxide. The invention is illustrated by the following examples, which must not however be considered as limiting thereof.

EXAMPLE 1

3 l of methanol and 480 g of CuCl are fed into an autoclave lined internally with a ceramic material.

The system is raised to a temperature of 120° C., and a gaseous stream containing CO and $H_2$ of which the hydrogen occupies 33% by volume is fed in at a flow rate of 140 Nl/hr simultaneously with a gaseous oxygen stream at a flow rate of 40 Nl/hr, under a total pressure of 25 kg/cm².

70 Nl/hr of gas consisting of $H_2$ (65%), CO (32%), $CO_2$ (3%) and $O_2$ (0.1–0.2%) are bled continuously from the system. After 4 hours, the methanol conversion is 32.5%, with the dimethylcarbonate selectivity being 100% with respect to the methanol and 95% with respect to the carbon monoxide.

EXAMPLE 2

3 l of methanol and 480 g of CuCl are fed into an autoclave having a capacity of about 6 liters. The system is raised to 70° C. and $O_2$ is fed in intermittently at 4 kg/cm² until the copper is completely oxidised (about 30 minutes).

The excess oxygen is bled off, the temperature raised to 120°, and a mixture of CO and $H_2$ containing 33% of hydrogen by volume is fed into the autoclave intermittently in such a manner as to keep the system at a pressure of 25 kg/cm².

93 Nl of mixture are fed in total.

The reaction is complete in about 20 minutes. The analysis of the liquid at the end of the reaction indicates the formation of dimethylcarbonate (8.20% by weight) and water (1.8%) with a dimethylcarbonate selectivity of 93% with respect to the carbon monoxide and total with respect to the methanol. Analysis of the gas at the end of the reaction indicates a composition of 20% v/v CO, 7% $CO_2$, 73% $H_2$. A further three cycles of oxidation-reduction are carried out in the same manner as heretofore described, obtaining a substantially similar behaviour except for a slight increase in the $CO_2$ and in the reaction time.

At the end of the four cycles, the liquid phase contains 28.9% of dimethylcarbonate and 5.9% of water.

EXAMPLE 3

A mixture of methanol (1670 g, 67%), dimethylcarbonate (740 g, 30%) and water (65 g, 2.7%) is fed into the apparatus of example 1 together with 480 g of cuprous chloride. The system is raised to a temperature of 120°, and a mixture of CO and $H_2$ containing 33% v/v of $H_2$ is fed in at a flow rate of 130 Nl/hr simultaneously with an oxygen stream at a flow rate of 30 Nl/hr, under a total pressure of 25 kg/cm$^2$.

80 Nl/hr of gas having a composition of 40% CO, 53% $H_2$, 7% $CO_2$ and 0.2% $O_2$ are bled off continuously.

After two hours of reaction, an analysis of the liquid phase indicates a composition of 51% $CH_3OH$ by weight, 43% dimethylcarbonate, 6% $H_2O$, with a selectivity of 100% with respect to the methanol and 89% with respect to the carbon monoxide (methanol conversion 16.5%).

After 4 hours, analysis indicates a composition of 38% $CH_3OH$ by weight, 54% dimethylcarbonate, 8% $H_2O$ (methanol conversion 35%).

EXAMPLE 4

The test described in example 1 is repeated using a mixture of CO and $H_2$ containing 33% v/v of hydrogen at a flow rate of 115 Nl/hr, maintaining the oxygen flow rate at 40 Nl/hr, under a total pressure of 25 kg/cm$^2$ at a temperature of 135° C. The gas continuously bled off from the system contains 8% CO, 84% $H_2$, 8% $CO_2$ and 0.4 $O_2$, and dimethylcarbonate is produced in the solution (approximately 90 g. liters/hr) with 100% selectivity with respect to the methanol and 94% with respect to the carbon monoxide.

EXAMPLE 5

The test described in example 1 is repeated using a mixture of CO and $H_2$ containing 10% v/v of hydrogen at a flow rate of 85 Nl/hr, while maintaining the oxygen flow rate at 40 Nl/hr, under a total pressure of 15 kg/cm$^2$ and at a temperature of 90° C. A gas containing 49% $H_2$, 33% CO, 18% $CO_2$ and 0.2% $O_2$ is continuously bled off at a flow rate of 18 Nl/hr, and dimethylcarbonate forms in the liquid phase at a rate and selectivity analogous to those of the preceding tests.

EXAMPLE 6

The test described in example 1 is repeated using a mixture of CO and $H_2$ containing 67% v/v of hydrogen at a flow rate of 250 Nl/hr, while maintaining the oxygen flow rate at 40 Nl/hr, under a total pressure of 50 kg/cm$^2$ and at a temperature of 135°.

A gas containing 91% v/v $H_2$, 7% CO, 2% $CO_2$ and 0.3% $O_2$ is bled off continuously at a flow rate of about 180 Nl/hr, and dimethylcarbonate is obtained in the liquid phase at a rate and selectivity analogous to those of the preceding tests.

EXAMPLE 7

The test described in example 3 is repeated at a flow rate of 390 Nl/hr for the CO/$H_2$ stream containing 33% of hydrogen, and a flow rate of 90 Nl/hr for the oxygen stream, under a total pressure of 35 kg/cm$^2$ and at a temperature of 120°.

The gas continuously bled off has a composition of 40% CO, 53% $H_2$, 6% $CO_2$ and 0.5% $O_2$.

After 1 hour of reaction, the analysis of the liquid phase indicates a composition of 49% $CH_3OH$ by weight, 45% dimethylcarbonate and 6% $H_2O$ (methanol conversion 20%).

We claim:

1. In a process for producing dimethylcarbonate by the reaction of methanol with oxygen and carbon monoxide in the presence of a copper salt catalyst, the improvement which comprises the utilization of a starting gaseous reactant containing hydrogen in addition to carbon monoxide and oxygen and the obtention of a by-product synthesis gas stream enriched in hydrogen content.

2. A process for producing dimethylcarbonate as claimed in claim 1, wherein the gaseous mixture fed into the methanol contains between 0.1 and 90% of hydrogen by volume.

3. A process for producing dimethylcarbonate as claimed in claim 1, wherein the reaction is carried out preferably within a temperature range of between 70° and 150° C.

4. A process for producing dimethylcarbonate as claimed in claim 1, wherein in carrying out the reaction the gaseous mixture fed into the methanol contains carbon monoxide at a partial pressure greater than atmospheric pressure.

* * * * *